United States Patent [19]

Iwasaki et al.

[11] Patent Number: 4,670,417

[45] Date of Patent: Jun. 2, 1987

[54] HEMOGLOBIN COMBINED WITH A POLY(ALKYLENE OXIDE)

[75] Inventors: Keiji Iwasaki; Yuji Iwashita, both of Kawasaki; Taketoshi Okami, Yokohama, all of Japan

[73] Assignee: Ajinomoto Co., Inc., Tokyo, Japan

[21] Appl. No.: 831,500

[22] Filed: Feb. 21, 1986

[30] Foreign Application Priority Data

Jun. 19, 1985 [JP] Japan ............................. 60-132056

[51] Int. Cl.$^4$ ..................... C07K 13/00; A61K 31/74; A61K 35/14
[52] U.S. Cl. ........................................ 514/6; 424/101; 530/385
[58] Field of Search ................... 260/112.5 R, 112 B; 424/101; 530/385; 514/6

[56] References Cited

U.S. PATENT DOCUMENTS

| | | | |
|---|---|---|---|
| 4,179,337 | 12/1979 | Davis et al. | ........................ 435/181 |
| 4,301,144 | 11/1981 | Iwashita et al. | ............ 260/112 B X |
| 4,412,989 | 11/1983 | Iwashita et al. | ......... 260/112.5 R X |
| 4,478,829 | 10/1984 | Landaburu et al. | ............ 424/101 X |
| 4,529,719 | 7/1985 | Tye | ............................. 260/112 B X |

Primary Examiner—Howard E. Schain
Attorney, Agent, or Firm—Oblon, Fisher, Spivak, McClelland & Maier

[57] ABSTRACT

There is disclosed hemoglobin modified in that a poly(alkylene oxide) is bonded thereto by a bond between a terminal group of said poly(alkylene oxide) and an amino group of said hemoglobin, said bond having the structure:

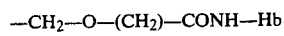

$$-CH_2-O-(CH_2)_n-CONH-Hb$$

wherein Hb represents said hemoglobin and n represents a positive integer, preferably 1 to 7. The modified hemoglobin is an effective oxygen carrier and can therefore be used as a blood substitute.

11 Claims, 1 Drawing Figure

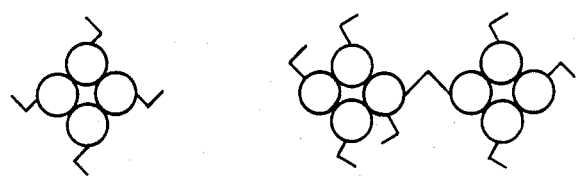
A    B
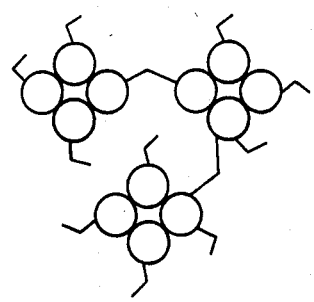
C

HEMOGLOBIN COMBINED WITH A POLY(ALKYLENE OXIDE)

BACKGROUND OF THE INVENTION

1. Field of the Invention

The present invention relates to hemoglobin combined with a poly(alkylene oxide), which is a novel combination and which is hereinafter referred to as "modified hemoglobin", for as an oxygen carrier in a blood substitute, and to lyophilized preparations containing the modified hemoglobin.

2. Description of the Prior Art

It has been reported that hemoglobin covalently combined with a poly(alkylene oxide) is excellent as an oxygen carrier in a blood substitute because the life time of this modified hemoglobin in the circulation is much longer than that of unmodified hemoglobin itself (see JP Nos. 12308/1981, 206622/1982, U.S. Pat. Nos. 4,301,144 and 4,412,989).

Hemoglobin is a constituent of the living body. However, there are the following problems in the modification of hemoglobin: (1) hemoglobin is denatured during reaction with a poly(alkylene oxide) and (2) the affinity of hemoglobin to oxygen is increased by the chemical modification. Moreover, the stability of the bonding between the hemoglobin and the poly(alkylene oxide) is not stable enough for the modified hemoglobin to be stored for an extended period of time.

SUMMARY OF THE INVENTION

The inventors of the present invention have tried to solve the above problems, and have found that hemoglobin combined with a poly(alkylene oxide), wherein an amino group of the hemoglobin is bonded via an amide bond to a carboxyl group of the poly(alkylene oxide), which carboxyl group is attached to the poly(alkylene oxide) molecule via an ether bond, can solve the above problems, and have devised the present invention on the basis of such findings.

In another words, the present invention relates to a hemoglobin modified in that it is combined with a poly(alkylene oxide), wherein the bond between said poly(alkylene oxide) and said hemoglobin is an amino group having the following structure:

wherein Hb represents a hemoglobin and n represents a positive integer.

BRIEF DESCRIPTION OF THE DRAWING

The singe FIGURE of the drawing shows typical instances of monomeric, dimeric and trimeric forms of modified hemoglobin of the invention. This FIGURE is referred to in Example 1 hereinbelow.

DESCRIPTION OF THE PREFERRED EMBODIMENTS

The poly(alkylene oxide) used in the present invention is a polymer having a solubility in water, for example, poly(ethylene oxide), poly(propylene oxide), or a copolymer of ethylene oxide and propylene oxide. The molecular weight of the polymer is preferably from 300 to 20,000, more preferably from 750 to 10,000, and most preferably from 1000 to 6000, from the point of view of the efficiency and safety of the final product.

In order to bond carboxylic groups to poly(alkylene oxide), ester bonds, amido bonds, ether bonds and the like can be considered. In the present invention, it has been found that an ether bond is better than the other bonds from the viewpoint of stability, and on the basis of these findings the present invention was made as mentioned above. Accordingly, in the case of the poly(alkylene oxide) used for synthesizing the conjugate of hemoglobin with the poly(alkylene oxide), of the present invention, the terminal groups thereof must be changed to a radical represented by the formula: $-O-(C-H_2)_n-COOH$ wherein a positive integer of from 1 to 10, preferably from 1 to 7, more preferable from 1 to 3, is selected for n in many cases.

As the method for changing the terminal groups of the poly(alkylene oxide) to a carboxyl alkylene ether group, (a) oxidation of the terminal carbon atoms of the poly(alkylene oxide) in the presence of a catalyst such as platinum, palladium or a combination of platinum and palladium, (b) oxidation of the terminal hydroxyl groups of the poly(alkylene oxide) in the presence of activated manganese dioxide to form an aldehyde derivative and subsequent oxidation of the formyl group of the derivative with hydrogen peroxide to form the carboxyl group, (c) condensation of the halogenated fatty acid with the poly(alkylene oxide) in the presence of a base, and (d) reaction of a fatty acid having a diazonium group with the poly(alkylene oxide), are preferably used.

For the reaction of the hemoglobin with the poly(alkylene oxide) into which carboxyl groups have been introduced, it is preferred that a poly(alkylene oxide) activated ester (which is obtained by reaction of the poly(alkylene oxide) with an activating agent used in an ordinary peptide synthesis such as N-hydroxy succinimide, N-hydroxy phthalimide p-nitrophenol or pentachlorophenol) be allowed to react with the hemoglobin, or that the poly(alkylene oxide) be heated with a halogenating agent such as thionyl chloride to form a poly(alkylene oxide) acid halide as a condensate be reacted with the hemoglobin.

The hemoglobin used in the present invention includes hemoglobin obtained from animals such as cattle, swine, sheep, horses, dogs, monkeys and chickens, as well as from human beings. The hemoglobin used in this invention includes the so called abnormal hemoglobin as disclosed in K. Imai, "Allosteric Effects in Haemoglobin", Cambridge University Press, 1980, and hemoglobin derivatives such as phosphate derivatives (for example pyridoxal-5'-phosphate and derivatives thereof, and 2-nor-2-formyl pyridoxal-5'-phosphate and derivatives thereof), pyridoxal sulfate derivatives (for example pyridoxal-5'sulfate and derivatives thereof), glyceric acid derivatives (for example 2,3-diphosphoglyceric acid and derivative thereof), derivatives obtained from a sugar containing a carboxylic acid or phosphate group (for example glucose-6-phosphate), and adenosine-5'-phosphate and derivatives thereof.

In the reaction of the hemoglobin, the concentration thereof is preferably from 0.5 to 20%, more preferably from 0.5 to 10% by weight/volume. However, when the concentration of the hemoglobin is over 4% and amino acids or amines are not present in the reaction system, a crosslinking reaction occurs which causes polymerization of the hemoglobin, and accordingly gelation of the reaction mixture often happens and the control of the reaction is very difficult. On the other hand, when the concentration of the hemoglobin is low, large reaction vessels must be used and concentration of the reaction mixture is time-consuming and energy-consuming. It is therefore preferred that from 1 to 50 mole, more preferably from 2 to 10 mole, of the poly(alkylene oxide) be used for one mole of the hemoglobin.

In the case of a reaction between the poly(alkylene oxide) and the hemoglobin in the presence of an amino acid or an amine, the molecular weight of the modified hemoglobin can be controlled easily. It is believed that an amino acid or amine attaches to part of the activated carboxyl group of the poly(alkylene oxide), and that the substance thus produced prevents excessive carboxyl groups from reacting with the hemoglobin. By this method, the modified hemoglobin of the present invention can be obtained easily without diluting the hemoglobin solution.

As an amino acid for use in the reaction, an amino acid constituting a protein is preferably used. Examples thereof are basic amino acids such as lysine, arginine and histidine, neutral amino acids such as glycine and phenylalanine, and acidic amino acids such as glutamic acid and aspartic acid. Examples of the amine are ammonia, aliphatic amines and aromatic amines. Since the modified hemoglobin is to be put into the blood circuit, the substance must be very safe. One amino acid or a combination of more than one amino acid or amine can be used for the reaction.

When an amino acid or amine whose amino group is a tertiary group is used, the carboxylic group of the poly(alkylene oxide) to be bonded to the hemoglobin has the formula $-O-(CH_2)_n-COOH$, because the tertiary amino group catalyzes hydrolysis of the activated ester. On the other hand, in the case of a primary or secondary amino group, the terminal group has the formula $-O-(CH_2)_n-CONHR$. By appropriately selecting the radical R, the degree of charge on the surface of the modified hemoglobin, or the hydrophobic or hydrophilic nature thereof, can be adjusted as required. Thus, when the modified hemoglobin is used as a blood substitute, the mutual interaction between the modified hemoglobin and red blood corpuscles, leucocytes and blood plasma proteins which are contacted by the modified hemoglobin in the living body can be regulated in respect of, for example, erythrocyte sedimentation rate and immuno-recognition.

It is preferred that from 1 to 100 mole, more preferably from 5 to 20 mole, of the amino acid for employed for one mole of the hemoglobin in the reaction.

In the reaction of the hemoglobin with the poly(alkylene oxide), the reaction system should not contain oxygen or should contain as low a volume of oxygen as possible. For example, an oxygen partial pressure of 0 to 30 mmHg is preferred. As regards reaction conditions other than the concentration of oxygen, all of the known art is applicable provided that the hemoglobin is not denatured.

In order to lower the concentration of the oxygen, the air in the reaction vessel can be replaced by an inert gas such as nitrogen, argon or helium. Alternatively, the oxygen can be removed by reducing it with a reducing agent such as $NaBH_4$ or $Na_2S_2O_4$, or it can be removed by a mechanical pump and replaced by an inert gas such as argon. Other known methods can be employed.

The modified hemoglobin thus obtained may be freeze-dried to form a preparation for use as a drug. A so-called stabilizing agent should be added to inhibit the production of methemoglobin and insoluble material. As stabilizing agents, we have examined anti-oxidizing agents such as sodium sulfite, sodium bisulfite and iron (II) sulfate, and amino compounds such as EDTA and salts thereof. However, inorganic anti-oxidizing agents are toxic to the human body and result in the production of large amounts of insoluble material. EDTA is not so effective from the viewpoint of stability for the long term preservation of the modified hemoglobin, because it does not effectively prevent the production of methemoglobin.

It is known that monosaccharides such as D-galactose and D-glucose and disaccharides such as sucrose and lactose are effective as stabilizing agents. However, they must be added in a relatively large amount relative to the modified hemoglobin, and therefore the concentration of blood sugar is increased and also the osmolarity of the solution is over the normal value. These effects are thought to be undesirable when the modified hemoglobin is to be used as a resuscitation fluid.

The present inventors found that glucose and mannitol are effective to prevent the formation of methemoglobin. They have attempted to develop preparations suitable for long term storage and have found that methemoglobin formation can be prevented effectively by using maltose and glucose as sugars during lyophilization of the modified hemoglobin.

As an example of a method of producing a freeze-dried preparation for use as a drug containing the modified hemoglobin of the present invention, an aqueous maltose solution or maltose powder is added to an aqueous solution of the modified hemoglobin, and the aqueous solution thus obtained is freeze-dried by a conventional method. As regards the amount of maltose to be mixed with the modified hemoglobin, 0.1 to 2.0 parts by weight of maltose is preferably employed per one part of weight of the modified hemoglobin. For example, having regard to stability, 0.1 to 2.0 times, preferably 0.5 to 1.2 times, of maltose is added to 2 to 20 w/v % of the modified hemoglobin solution and the mixture thus obtained is freezed at $-35°$ to $-50°$ C. for 20 to 60 minutes and then dried under reduced pressure at 10° to 50° C. on a shelf for 5 to 70 hours to give a freeze-dried preparation for a drug. It is preferred that an amino acid such as histidine, glutamine or tryptophan be added with the maltose and/or glucose, for the preparation of the drug.

Before the freezing of the aqueous modified hemoglobin solution containing maltose and/or glucose, known stabilizing agents and/or salts to adjust osmotic pressure of the crystalizing substance may be added.

The modified hemoglobin of the present invention possesses excellent properties such as the affinity of the hemoglobin for oxygen and also the high stability thereof.

In the case of, for example, poly(ethylene oxide), the following three terminal groups may be present:

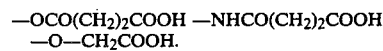
$-O-CH_2COOH.$

These kinds of terminal groups may be combined with the hemoglobin. As regards the three kinds of modified hemoglobin thus obtained, their resistance to hydrolysis was examined and the results were compared as follows.

5% Aqueous solutions (pH 7.0, 0.1N phosphate buffer) of each of the modified hemoglobins of ester type (I), amide type (II) and ether type (III) as given above were incubated at 35° C. for one week, and the poly(ethylene oxide) produced by the decomposition of the modified hemoglobins was measured. It was found that the order of the hydrolyzed poly(ethylene oxides) was III>II>I> by weight. Judging from these results, the ether type had the best stability. Also, in the production of the freeze-dried preparation of the modified hemoglobin, when lyophilization is carried out in the presence of maltose, the maltose prevents the modified hemoglobin from undergoing oxidation.

The present invention will be illustrated by the following Examples.

In these Examples, the molecular weight of the product was determined by high speed liquid chromatography, combined with small angle light scattering. As the developing solvent, 0.1M phosphate buffer (pH=6.8) was employed. The molecular weight was calculated by the following method. A calibration curve is obtained by using a gel type packed column (SW3000G, Toya Soda Co. Inc., Japan) and by analyzing the small angle laser scattering (LC-8, Toyo Soda Co. Inc., Japan) of the chromatogram.

The number of poly(alkylene oxide) moleclues which combined with one molecule of hemoglobin was determined as follows. Salts and unreacted poly(alkylene oxide) were completely removed by ultrafiltraton, and a solution of the product was freeze-dried. The solid residue was weighed, and then the hemoglobin content in the solid residue was determined photometrically. The number of combined poly(alkylene oxide) molecules was calculated by subtracting the volume of the hemoglobin in the relevant sample.

The oxygen dissociation curve of the stabilized hemoglobin thus obtained was measured in 0.1M phosphate buffer (pH=7.4) by the method of Imai et al (K. Imai, H. Morimoto, M. Kotani, H. Waka, M. Kuroda, Biochim. Biophys. Acta., 200, 189–196, 1970).

EXAMPLE 1

Poly(ethylene oxide) having a molecular weight of 1000 daltons, produced by Aldrich Chemical Co., USA (30 g, 30 mmole), and 3-chloropropionic acid ethylester (16.4 g, 120 mmole) were dissolved in dried dimethylformamide (700 ml), and silver oxide (20 g) was added thereto. The mixture was stirred for 24 hours at 70° C. to effect a reaction, and the precipitate thus obtained was removed by filtration. The filtrate thus obtained was poured into cooled ethyl ether (3 liters) to precipitate the desired poly(ethylene oxide) derivative. The precipitate was washed with ethyl ether, dried, and dissolved again in water (300 ml). The solution was adjusted to a pH above 11 with 1N aqueous sodium hydroxide and then stirred overnight at 60° C. to hydrolyze the ester. The pH of the reaction solution was adjusted with 1N aqueous hydrochloric acid to a value of 5 and then the solution was concentrated and dried to give a solid material.

The product thus obtained was dissolved in a mixture (200 ml) of methylene chloride and ethyl ether (1:1) and insoluble material was removed by filtration. The filtrate was concentrated to precipitate a white powder. The powder was dissolved in water (100 ml), and the aqueous solution was treated with a strongly basic ion exchange resin, namely "Bio-Rad" AG1X2 produced by Bio-Rad Laboratories, USA, and the adsorbed material was eluted with 0.05N aqueous hydrochloric acid. The yield of product was 18 g, the product being in the form of white crystals.

The product (i.e. the dicarboxylic acid derivative of the poly(ethylene oxide) (10 g) and N-hydroxysuccinimide (6.5 g, 56.5 mmole) were dissolved in dimethylformamide (200 ml), and then dicyclohexylcarbodiimide was poured into the mixture to effect a condensation reaction thereby to obtain an activated ester of the poly(ethylene oxide) derivative having a molecular weight of 1000 in a yield of 9.8 g.

Fresh erythrocytes from a cow (100 ml) were suspended in a 0.9% aqueous sodium chloride solution and washed four times at 4° C. using a centrifuge. The erythrocytes thus washed (60 ml) were hemolized with 60 ml of distilled water suitable for injection. The membrane components of the erythrocytes were removed using a filter having a hole diameter of 0.22 microns, produced by Millipore Co., USA. The remaining membrane components were removed by centrifugation at 6000 r.p. for 1 hour.

The bovine hemoglobin solution thus obtained (10 g) was dissolved in 0.1M borate buffer (pH 7.0, 200 ml), and to the solution thus obtained (0.15 mmole) the foregoing activated poly(ethylene oxide) ester (4.7 g, 3.5 mmole) and L-lysine (212 mg, 1.45 mmole) were added. The oxygen partial pressure in the reaction mixture was reduced to 1 mmHg with argon gas. The mixture was reacted for 2 hours at 4° C.

The reaction mixture was purified repeatedly by ultrafiltration using the membrane YM-10 produced by Amicon Co., USA until the amount of unreacted poly(ethylene oxide) was less than 100 ppm. Unmodified hemoglobin was not present in the purified mixture, according to a gel filtration chromatography test. As can be seen from the FIGURE, a product of monomeric type (A), a product of dimeric type (B) and a product of trimeric type (C) were produced. The ratio of these three types was about 5:3:1. In the FIGURE, each circle represent a subunit of one hemoglobin molecule and each hook shaped member represents a poly(ethylene oxide)molecule.

The average number of poly(ethylene oxide)-molecules which combined with one hemoglobin molecule was 6.3.

The oxygen partial pressure at which half of the oxygen was combined with the chemically modified hemoglobin ($P_{50}$ value) in an oxygen dissociation curve was 13.7 mmHg at 25° C. From an analysis of the product it was clear that the L-lysine radical was bonded to the poly(ethylene oxide) via an amide bond.

EXAMPLE 2

An aqueous solution (500 ml) of platinum-palladium-carbon (20 g) as a catalyst, produced by the method disclosed in JP No. 141219/1978 (Kawaken Fine Chemical Co., Inc.), and a poly(ethylene oxide) (200 g) made by Nihon Yushi Co., Inc., Japan, namely Macrogol 4000, were placed in an autoclave and pressured air was fed into the autoclave to adjust the pressure to 10 kg/cm$^2$. The mixture was reacted for 10 hours at 90° C.

The catalyst was removed by filtration from the reaction solution. The solution thus obtained was treated with activated carbon and then recrystallized from water to obtain an acid derivative of poly(ethylene oxide) having carboxyl groups at both ends thereof, in a yield of 180 g.

α-Carboxymethoxy, ω-carboxymethyl polyoxyethylene (molecular weight about 4000) (20 g, 5 mmole), N-hydroxysuccinimide (4 g), and dicyclohexylcarbodiimide (DCC) (7 g) were dissolved in dimethylformamide (100 ml) and stirred overnight. The crystals of dicyclohexyl urea that formed were separated by filtration. To the filtrate, ethyl ether (400 ml) was added to precipitate a polyoxyethylene derivative of the activated ester (17 g). The precipitate was separated by filtration and then washed with ethyl ether.

Human erythrocyte (50 ml) which had been obtained from outdated blood for transfusion was washed with 0.9% aqueous sodium chloride solution (50 ml), four times at 4° C. using a centrifuge.

The washed erythrocyte (40 ml) was hemolized with distilled water suitable for injection (40 ml). The membrane components of the erythrocyte were extracted with toluene (20 ml). Furthermore, the membrane components of the membrane and the human hemoglobin were separated by centrifugation at 8000 r.p. for 1 hour to obtain a hemoglobin solution.

The hemoglobin solution was dissolved in 0.1M phosphate buffer (0.088 mmole, pH 7.0) to adjust the concentration of the hemoglobin to 6 g/dl, and then the partial oxygen pressure was lowered to less than 2 mmHg by vigorously blowing argon gas into the hemoglobin solution (100 ml) to remove oxygen therefrom. According to the method of Benesch et al (R. Benesch, R. Benesch, S. Kwong, A. Acharya, J. Manning, J. Biol. Chem. 257 (13) 1320-1324, 1982), pyridoxal-5'-phosphate was attached to the hemoglobin to obtain pyridoxalated hemoglobin (6 g/dl). Glycine (160 mg) was added thereto and the activated ester of the polyoxyethylene derivative (7.2 g) obtained in the manner described above was added thereto. The mixture was reacted for 30 minutes at 4° C. 1N aqueous sodium hydroxide was added thereto to adjust the pH value to 7.8, and then the solution was further reacted for 30 minutes.

The product was purified by repeated ultrafiltration using a membrane whose molcular weight cut-off point was 30,000 daltons (Membrane YM30, Amicon Co. Inc., USA), whereby the concentration of unreacted polyoxyethylene was less than 100 ppm.

The average molecular weight of the product was estimated to be about 98,000 daltons (by high speed liquid chromatography using a column filled with the gel of the same type as described above and by subsequent analysis by small angle laser scattering). Glycine was bonded to those terminal groups of the polyethylene glycol to which hemoglobin was not attached.

To a 6.0% aqueous solution of the modified hemoglobin thus produced, a solution of salts (a mixture of sodium chloride, potassium chloride, sodium acetate and/or mognesium chloride), and a glucose or maltose solution were added to produce modified hemoglobin solutions having a hemoglobin concentration of 5%, and having various sugar concentrations as shown in Table 1. They were freeze-dried by conventional means for 18 hours at 20° C. on a shelf to produce preparations.

The degree of methemoglobin to total hemoglobin (which is referred to as "methemoglobin content degree") of these preparations just after freeze-drying and after preservation at 30° C., is given in Table 1. As a result, it can be seen that maltose is superior to glucose as a stabilizing agent. Particularly, it is effective in a concentration of 4 to 6% (about 0.8 to 1.2 times relative to the modified hemoglobin).

TABLE 1

| Yield of methemoglobin in preservation tests carried out on freeze-dried preparations containing glucose or maltose as a stabilizing agent 30° C. | | | |
|---|---|---|---|
| Stabilizing Agent | Starting Value | After 7 days | After 14 days |
| Glucose 3% | 1.3% | 10.1% | 15.3% |
| Glucose 4% | 1.4% | 9.5% | 13.4% |
| Maltose 3% | 1.2% | 5.4% | 8.8% |
| Maltose 4% | 1.3% | 4.6% | 7.9% |
| Maltose 5% | 1.2% | 3.9% | 5.2% |

EXAMPLE 3

Commerically-available Pluronic P123 of molecular weight 4000 daltons (a block copolymer of ethylene oxide and propylene oxide) (20 g, 5 mmole), produced by BASF Wayandotte Co., USA, was reacted with metallic sodium (1 g) in well-dehydrated dioxane to give the disodium salt of pluronic P123. The precipitate thus obtained was separated by filtration, and to the filtrate monochloroacetic acid ethylester (2 ml) was added dropwise. The mixture was reacted for 24 hours at 50° C.

By the method as described in Example 1, from the reaction solution thus obtained, the ester derivative was hydrolyzed to produce a precipitate. This process was repeated to purify the required product.

The resulting poly(alkylene oxide) derivative, wherein both ends of the Pluronic molecule possess carboxyl groups, was reacted with N-hyroxysuccinimide using the method described in Example 2 to convert it to the activated ester derivative.

Into 6% aqueous human hemoglobin (0.09 mmole, 100 ml) in a borate buffer (pH 7.4), obtained by the method described in Example 2, nitrogen gas was blown to lower the partial oxygen pressure thereof to 1 mmHg. Then, the activated ester of Pluronic (7 g, 1.7 mmole) as obtained above and L-alanine (250 mg, 2.8 mmole) was added. The mixture was reacted for 1 hour at 4° C. The pH of the solution was adjusted to 7.8, and then the mixture was stirred for 30 minutes. The required product was obtained by purification, by the method described in Example 1.

The average molecular weight, as estimated by the method described in Example 1, was 95,000 daltons. The number of Pluronic molecules which combined with one hemoglobin molecule was 4.8. The P50 value, at which pressure half of the oxygen was dissociated, as estimated from the oxygen dissociation curve, was 6.1 mmHg at 25° C.

EXAMPLE 4

Polyethylene glycol monomethyl ether having a molecular weight of 1900 (15 g, 7.9 mmole) made by Aldrich Chemical Co., USA was dissolved in dried methylene chloride, and activated manganese dioxide (30 g) was added thereto. The mixture was stirred overnight at room temperature to effect reaction.

After the catalyst had been separated by filtration, the polyethylene glycol derivative, oxidized to one of aldehyde type, obtained by distilling off the solvent under reduced pressure from the above solution, was dissolved in 3% aqueous hydrogen peroxide ($H_2O_2$) solution (500 ml). The mixture was allowed to react for 24 hours.

The reation solution was passed through a column packed with the resin Bio-Rad AG1x2 to remove neutral material, and a poly(ethylene oxide) derivative having a terminal carboxyl group was obtained by eluting the column with 0.02M aqueous hydrochloric acid solution.

This acid derivative (5 g, 2.6 mmole) was dissolved in dried dimethylformamide (100 ml), and N-hydroxysuccinimide (0.8 g, 7.0 mmole) and dicyclohexylcarbodiimide (1.5 g, 7.2 mmole) were added thereto. The mixture was reacted overnight at room temperature.

Insoluble material was separated by filtration, and to the filtrate thus obtained dried ethyl ether was added to produce a precipitate of the activated ester.

A 6% aqueous solution of human hemoglobin (300 ml), produced by the method described in Example 2, was reacted with glyoxalic acid in a 20-fold excess volume of HEPES buffer, by the method of Didonato et al (A. DiDonato, W. Fartl, A. Acharya, J. Manning, J. Biol. Chem., 258 11890-11895, 1983) and the product thus obtained was reduced with $NaBH_3CN$.

Low molecular material was removed with "Sephadex G-100" from the carboxymethylated hemoglobin thus obtained, and 0.1M phosphate buffer was added thereto to dilute the solution to 5.2 g of hemoglobin per 100 ml. The solution was reacted with the polyethylene glycol monomethyl ether activated ester (4.8 g) obtained by the method described above for 2 hours at 5° C.

The product was purified by the ultrafiltration method described in Example 1. The average molecular weight, as determined by the method described above, was 82000 daltons. The $P_{50}$ value was 12 mmHg at 25° C. (pH 7.4).

EXAMPLE 5

The process of Example 2 was repeated except that poly(ethylene oxide) having a mean molecular weight of 8000 daltons (20 g, 2.5 mmole), made by Aldrich Chemical Co., USA, was employed as a starting material to obtain a carboxylic acid derivative wherein both ends of the poly(ethylene oxide) have an —O—CH$_2$—CO$_2$H radical.

The carboxylic acid derivative, purified with the resin Bio-Rad AG1X2, was reacted with N-hydroxysuccinimide in the same manner as in Example 2 to give an activated ester.

Bovine hemoglobin (7 g), as obtained by the method described in Example 1, in the form of 0.1M solution thereof (100 ml) in a phosphate buffer (pH 7.4), was reacted with pyridoxal-5'-phosphate by the method of Benesch referred to above, and successively reduced with sodium borohydride (NaBH$_4$).

Into the above solution, highly purified nitrogen gas was blown to remove oxygen from the solution, and then N-dimethylglycine (1500 mg) and the above described activated ester of the polyoxyethylene derivative (4.8 g) were added. The mixture was reacted for 1 hour at a temperature of 4° C.

Using the method described in Example 1, the reaction mixture was purified by removing low molecular weight material.

By the cyanomethemoglobin method, the concentration of the hemoglobin was determined, and thereby it was found that the yield was 63% based on the bovine hemoglobin. The mean molecular weigth was 20,000 daltons. The viscosity of a solution having a hemoglobin concentration of 6% was 2.8 cps. The $P_{50}$ value was 19 mmHg at 25° C. (pH 7.4) from the oxygen dissociation curve, as measured by the method of Imai described above.

To the above described standard modified hemoglobin solution (concentration of hemoglobin: 6.0%) (100 ml), maltose in an amount (3.4 g) which corresponds to 0.56 times by volume of the hemoglobin, and the salts given in Example 2 were added to adjust the osmotic pressure to 280 mOsmol, in the same manner as in Example 2. The preparations thus produced were preserved at 10° C. and the results thus obtained are given in Table 2. These results shown that the modified hemoglobin to which maltose and the salts had been added were very stable.

| Effect of salts and maltose upon lyophilized modified hemoglobin (preservation at 10° C.) | | | | | | | |
|---|---|---|---|---|---|---|---|
| Number of months of preservation | 0 | 1 | 2 | 3 | 4 | 5 | 6 |
| Methemoglobin content (%) | 2.92 | 5.96 | 7.83 | 8.98 | 10.75 | 11.24 | 12.12 |

The modification of hemoglobin with a poly(alkylene oxide) in accordance with the present invention does not denature the hemoglobin, and does not harm its affinity for oxygen. Moreover, the modified hemoglobin has a high stability and maintains its activity for long times both during the making of preparations therefrom and during storage thereof. The stability from the preparation stage to the storage stage is further improved by the addition of maltose as a stabilizing agent.

These materials can be expected to be a virus-free oxygen carrier.

We claim:

1. A modified hemoglobin, comprising: hemoglobin bonded to the terminal groups of poly(alkylene oxide) through the amino groups in said hemoglobin by a linking group of the structure: —CH$_2$—O—(CH$_2$)$_n$—CONH—Hb, wherein Hb represents said hemoglobin and n is a positive integer.

2. The modified hemoglobin according to claim 1, wherein said linking group, prior to reaction with the amino groups of said hemoglobin, is a free carboxylic acid of the formula: —OCO(CH$_2$)$_2$COOH, —NHCO(CH$_2$)$_2$COOH or —O—CH$_2$COOH, which is linked to said poly(alkylene oxide).

3. The modified hemoglobin according to claim 1, wherein at least 50% of the terminal groups of said poly(alkylene oxide) not bonded to said hemoglobin are bonded to an amino acid radical by an amide bond.

4. The modified hemoglobin according to claim 3, wherein said amino acid is selected from the group consisting of natural amino acids that constitute a protein.

5. The modified hemoglobin according to claim 1, wherein said poly(alkylene oxide) is selected from the group consisting of poly(ethylene oxide), poly(propylene oxide) and copolymers of ethylene oxide and propylene oxide.

6. The modified hemoglobin according to claim 1, wherein said poly(alkylene oxide) has a molecular weight of from 1000 to 6000.

7. The modified hemoglobin according to claim 1, wherein said modified hemoglobin is lyophilized with a sugar selected from the group consisting of maltose, glucose, and mixtures of maltose and glucose.

8. The modified hemoglobin according to claim 1, wherein n is an integer of from 1 to 10.

9. The modified hemoglobin according to claim 8, wherein n is an integer of from 1 to 7.

10. An effective oxygen carrier for use as a blood substitute, comprising:

a modified hemoglobin, as the oxygen carrying ingredient, which has the structure of hemoglobin bonded to the terminal groups of poly(alkylene oxide) through the amino groups in said hemoglobin by a linking group of the structure: $-CH_2-O-(CH_2)_n-CONH-Hb$, wherein Hb represents said hemoglobin and n is a positive integer.

11. A method of enhancing the oxygen carrying ability of blood, comprising:

injecting into the circulatory system of a subject, a modified hemoglobin bonded to the terminal groups of poly(alkylene oxide) through the amino groups in said hemoglobin by a linking group of the structure: $-CH_2-O-(CH_2)_n-CONH-Hb$, wherein Hb represents said hemoglobin and n is a positive integer.

* * * * *